United States Patent [19]

Aichinger et al.

[11] Patent Number: 5,225,574

[45] Date of Patent: Jul. 6, 1993

[54] PREPARATION OF PHTHALIC ANHYDRIDE FROM O-XYLENE

[75] Inventors: Heinrich Aichinger, Mannheim; Wilhelm Ruppel, Schwetzingen; Rolf Seubert, Frankenthal; Karl-Heinz Boehning, Ludwigshafen; Walter Scheidmeir, Limburgerhof; Johannes E. Schmidt, Ludwigshafen; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 682,295

[22] Filed: Apr. 9, 1991

[30] Foreign Application Priority Data

Apr. 24, 1990 [DE] Fed. Rep. of Germany ....... 4013051

[51] Int. Cl.$^5$ ............................................ C07D 307/89
[52] U.S. Cl. .................................... 549/248; 549/247; 549/257; 549/259; 549/260
[58] Field of Search ............... 549/248, 249, 257, 247, 549/259, 260

[56] References Cited

U.S. PATENT DOCUMENTS

| | | | |
|---|---|---|---|
| 3,684,741 | 8/1972 | Friedrichsen et al. | 252/435 |
| 3,871,445 | 3/1975 | Wanka et al. | 165/107 |
| 4,077,136 | 2/1977 | Blechschmitt et al. | 252/435 |
| 4,077,984 | 5/1978 | Blechschmitt et al. | 252/435 |
| 4,096,094 | 6/1978 | Blechschmitt et al. | 252/440 |
| 4,203,906 | 5/1980 | Takada et al. | 568/479 |
| 4,256,783 | 3/1981 | Takada et al. | 422/197 |
| 4,356,112 | 10/1982 | Nakanishi et al. | 252/435 |
| 4,411,818 | 10/1983 | Reuter et al. | 502/35 |
| 4,835,126 | 5/1989 | Wachs et al. | 502/209 |
| 4,849,391 | 7/1989 | Riva et al. | 502/202 |
| 4,870,195 | 9/1989 | Riva et al. | 549/248 |

FOREIGN PATENT DOCUMENTS

| | | |
|---|---|---|
| 1442590 | 10/1968 | Fed. Rep. of Germany . |
| 2201528 | 11/1972 | Fed. Rep. of Germany . |
| 2212947 | 9/1973 | Fed. Rep. of Germany . |
| 2546268 | 4/1977 | Fed. Rep. of Germany . |
| 2830765 | 1/1980 | Fed. Rep. of Germany . |

OTHER PUBLICATIONS

Chemical Abstracts vol. 90, entry 152 625, 1979.
Optimal Policies in Maleic Anhydride Production Through Detailed Reactor Modelling Wellauer et al., Chem. Eng. Sci. 41, 765 (1986).

Primary Examiner—Cecilia Tsang
Attorney, Agent, or Firm—Keil & Weinkauf

[57] ABSTRACT

Phthalic anhydride is prepared in a multiple tube reactor provided with separate salt baths, the temperature of the salt bath used for cooling the first layer of catalyst, as regarded in the direction of flow of the reaction mixture, being from 2° to 20° C. higher than that of the salt bath(s) associated with the following layer(s).

3 Claims, No Drawings

PREPARATION OF PHTHALIC ANHYDRIDE FROM O-XYLENE

The invention relates to an advantageous process for the preparation of phthalic anhydride by catalytic gas-phase oxidation of o-xylene using supported catalysts containing vanadium pentoxide, titanium dioxide, antimony, rubidium, and/or cesium, and/or phosphorus in two or more reaction zones, in which the temperature of the salt bath in the first reaction zone is higher than that in the second or following reaction zones.

A known method of manufacturing phthalic anhydride on an industrial scale comprises subjecting o-xylene to catalytic air-oxidation in a fixed-bed reactor. Suitable catalysts for this process are, in particular, supported catalysts consisting of, say, spherical inert supports coated with a thin layer of catalytically active material comprising vanadium pentoxide and titanium dioxide. Such catalysts are described in DE-A 1,442,590 for example. Use has also been made of supported catalysts in which the catalytically active material is doped with phosphorus (U.S. Pat. No. 3,684,741) or with rubidium and/or cesium (U.S. Pat. No. 4,007,136 and U.S. Pat. No. 4,096,094).

In such prior processes the general procedure is to pass a mixture consisting of an oxygen-containing carrier gas, such as air, and the hydrocarbon to be oxidized through a plurality of tubes disposed in the reactor and containing the catalyst. Temperature control is effected by surrounding the tubes with molten salt kept at a temperature of from 350° to 420° C. This procedure produces undesirable by-products which are difficult to separate from the desired phthalic anhydride and thus impair the quality of the phthalic anhydride. The main impurity formed in the production of phthalic anhydride from o-xylene is phthalide.

The formation of this by-product increases with a rise in the concentration in the air of the hydrocarbon being treated. However, high concentrations of said hydrocarbon in the air are desirable for economic production. By high concentrations we mean concentrations exceeding the lower explosion limit of the hydrocarbon/air mixture, for example concentrations ranging from 44 to 100 g of xylene per m$^3$ of air.

The formation of by-products can be inhibited, for example, by carrying out the oxidation at a lower gas throughout (=longer sojourn time) or at a lower concentration of the hydrocarbon in the air. However, this leads to a drop in the yield of phthalic anhydride and in the reactor output.

An improvement in the production of phthalic anhydride by oxidizing o-xylene in air has thus been achieved by using at least two different catalysts in each reactor tube (DE-A 2,546,268). In this process o-xylene and air are passed at a temperature of from 350° to 500° C. over a catalyst bed in which the first zone encountered by the o-xylene/air mixture comprises from 25 to 50% v/v of the total of catalyst and contains catalyst having rubidium or cesium but no phosphorus in the catalytically active material, whilst the remaining zone contains catalyst having phosphorus but no rubidium or cesium in the catalytically active material. This process effects catalytic oxidation of the hydrocarbon for example in known manner in a multiple tube reactor employing salt bath cooling at a salt bath temperature of from 350° to 500° C. and preferably from 350° to 400° C. The reactor tubes surrounded by the salt bath have a diameter of from 18 to 40 mm and a length of from 2 to 3.5 m and are filled with the catalyst. This is a supported catalyst consisting of a catalytically inert support having a diameter of from 3 to 13 mm and coated with a thin layer of catalytically active material. The support is in the form of, say, spheres or, preferably, rings. The support is composed of sintered or molten silicate, porcelain, alumina, silicon carbide, or quartz. The catalytically active material forming a 0.05 to 1 mm thick coating on the support is composed of, say, from 1% to 30% w/w of vanadium pentoxide and from 70% to 99% w/w of titanium dioxide. If desired, it may contain small amounts, for example amounts not exceeding 5% w/w based on the catalytically active material, of antimony, zirconium, or of tin, phosphorus, rubidium, or of cesium, for example in the form of their oxides. The catalytically active material forms approximately 3% to 50% w/w of the supported catalyst.

This process involves the use of two or more different catalysts contained in a multiple tube reactor which is undivided with respect to the salt bath circulation and thus to temperature control, the tubes being surrounded by molten salt having a uniform temperature of from 350° to 420° C.

Now that reactors having two or more salt bath stages and containing tubes of different sizes are available as compact industrial units (cf. DE-A 2,201,528) for example, a reaction tube can be subdivided into two or more sections each having its own salt bath temperature, tube diameter, and catalyst packing.

Accordingly, processes for conducting a reaction using two salt bath circuits have been proposed for the oxidation of n-butane to maleic anhydride (Wellauer et al. in *Chem. Eng. Sci.* 41, 765, 1986) and for the oxidation of o-xylene to phthalic anhydride (DE-A 2,830,765). In both cases, however, the temperature at the output of the reactor must of necessity be higher than the temperature at the input of the reactor, that is to say, the temperature of the salt bath must be lower in the first reaction zone than in the second reaction zone. However, working according to the specifications of the above patent using commercial catalysts has not provided any improvement over the single-stage procedure.

We have now found that, in a process for the preparation of phthalic anhydride by oxidation of o-xylene in a multiple tube reactor incorporating at least two adjacent in-line reaction zones having separate salt bath cooling means and packed with supported catalysts coated with catalytically active materials containing vanadium pentoxide, titanium dioxide, antimony, rubidium, and/or cesium, and/or phosphorus, a mixture of o-xylene and air being passed over said catalysts at a temperature of from 320° to 380° C., improved yields are, surprisingly, obtained when the temperature of the salt bath used for the first reaction zone, as regarded in the direction of flow of the reaction mixture and comprising from 30% to 75% v/v of the total catalyst, is from 2° to 20° C. higher than the temperature of the salt bath(s) used for the remaining reaction zone(s) comprising from 25% to 70% v/v of the total catalyst, wherein the temperature of the salt bath used for the first reaction zone is adjusted to such a value, within the overall range of 320°–380° C., that virtually complete conversion, e.g. more than 99.5% conversion, of the o-xylene is achieved with maximum yield thereof.

According to a preferred embodiment of the invention, use is made of two reaction zones cooled by separate salt baths, the temperature of the salt bath used for the first reaction zone being preferably from 2° to 15° C. and more preferably from 5° to 15° C. higher than that of the second salt bath.

The catalysts used in the reaction zones are for example the prior catalysts containing vanadium pentoxide on a non-porous inert support such as are described in the patents referred to above (which are incorporated herein by reference). When, according to another preferred embodiment, two different catalysts are used in the adjacent in-line reaction zones, the catalyst in the first reaction zone advantageously additionally contains rubidium and/or cesium, as described in U.S. Pat. No. 4,007,136, while the catalyst in the second reaction zone advantageously additionally contains phosphorus, as described in U.S. Pat. No. 3,684,741. For the sake of simplicity, reference is made to the above two patents for further details.

As mentioned above, the process of the invention is particularly advantageous when the concentration of the o-xylene in the air is above the lower explosion limit, i.e. above 44 g/m$^3$ of air, and most particularly when it is 60 g/m$^3$ or more.

EXAMPLES

Manufacture of Catalyst I

Catalyst I consists of steatite balls having a diameter of 4.3 mm and coated with a 0.1 mm thick layer of catalytically active material. The catalytically active material is applied as specified in the Examples of U.S. Pat. No. 4,096,094 and consists of 7.00% w/w of vanadium pentoxide, 2.5% w/w of antimony oxide, and 0.16% w/w of rubidium. The remainder of the catalytically active material is titanium dioxide (anatase).

Manufacture of Catalyst II

Catalyst II consists of steatite balls having a diameter of 4.3 mm coated with a 0.1 mm thick layer of catalytically active material. The catalytically active material is applied as specified in the Examples of U.S. Pat. No. 4,096,094 and consists of 7.00% w/w of vanadium pentoxide, 2.5% w/w of antimony oxide, and 0.5% w/w of phosphorus. The remainder of the catalytically active material is titanium dioxide (anatase).

Oxidation

A multiple tube reactor in which the tubes have a length of 1.95 m and an internal diameter of 15 mm and which is divided into two sections having separate salt baths is filled with catalyst I over a distance of 0.9 m (first section of reactor as regarded in the direction of flow of the gaseous reaction mixture) and with catalyst II over a distance of 0.75 m (second section, below the first section). The reaction mixture having a concentration of o-xylene of about 60 g/m$^3$ (S.T.P.) of air is passed over catalysts I and II at a rate per unit catalyst (GHSV) of 2850$^{-1}$.

Comparative Example 1

In the above setup, the catalysts I and II were kept at the same reaction temperature. The results obtained are listed in the Table below.

| Reaction temperature [°C.] | o-Xylene concentration [g/m$^3$ of air (S.T.P.)] | Yield of PA* (following distillation) [% molar] |
| --- | --- | --- |
| 358 | 60 | 76.0 |
| 357 | 60 | 76.5 |
| 356 | 60 | 76.4 |

*phthalic anhydride

Comparative Example 2

In the above setup, the catalysts I and II were kept at different salt bath temperatures, the salt bath used for cooling catalyst I being at a lower temperature than that of the salt bath associated with catalyst II. The results obtained are listed in the Table below.

| Reaction temperature [°C.] | | o-Xylene concentration [g/m$^3$ of air (S.T.P.)] | Yield of PA (following distillation) [% molar] |
| --- | --- | --- | --- |
| Catalyst I | Catalyst II | | |
| 354 | 356 | 60 | 72.2 |
| 354 | 355 | 60 | 72.6 |
| 353 | 355 | 60 | 71.3 |
| 350 | 356 | 60 | incomplete xylene conversion |

Example of the Process of the Invention

In the above setup, the catalysts I and II were kept at different salt bath temperatures, the salt bath used for cooling catalyst I being at a higher temperature than that of the salt bath associated with catalyst II. The results obtained are listed in the Table below. The yields of phthalic anhydride were higher than those obtained in Comparative Example I in which both catalysts were maintained at the same salt bath temperature.

| Reaction temperature [°C.] | | o-Xylene concentration [g/m$^3$ of air (S.T.P.)] | Yield of PA (following distillation) [% molar] |
| --- | --- | --- | --- |
| Catalyst I | Catalyst II | | |
| 357 | 350 | 60 | 78.2 |
| 358 | 345 | 60 | 78.2 |
| 359 | 345 | 60 | 77.5 |
| 359 | 344 | 60 | 78.3 |
| 359 | 343 | 60 | 78.6 |
| 359 | 342 | 60 | 78.7 |

We claim:

1. A process for the preparation of phthalic anhydride by oxidation of o-xylene in a multiple tube reactor incorporating two adjacent in-line reaction zones having separate salt bath cooling means and packed with either the same supported catalyst or different supported catalysts coated with catalytically active materials containing vanadium pentoxide, titanium dioxide, antimony, rubidium, and/or cesium, and/or phosphorus, a mixture of o-xylene and air, in which the concentration of o-xylene is at least 60 g/m$^3$ of air, being passed over said catalyst at a temperature of from 320° to 380° C., wherein the temperature of the salt bath used for the first reaction zone, as regarded in the direction of flow of the reaction mixture and comprising from 30% to 75% v/v of the total catalyst, is from 2° to 20° C. higher than the temperature of the salt bath used for the second reaction zone comprising from 25% to 70% v/v of the total catalyst, wherein the temperature of the salt bath used for the first reaction zone is adjusted to such a value, within the overall range of 320°–380° C., that virtually complete conversion of the o-xylene is achieved with maximum yield thereof, and wherein different catalysts are used in the first and second reaction zones.

2. A process as defined in claim 1, wherein the catalyst associated with the second reaction zone additionally contains phosphorus as a catalyst component, wherein the catalyst associated with the first reaction zone does not.

3. A process as defined in claim 1, wherein the catalyst associated with the first reaction zone additionally contains rubidium and/or cesium as a catalyst component whereas the catalyst associated with the second reaction zone does not.

* * * * *